United States Patent
Gorr et al.

(10) Patent No.: US 10,822,628 B2
(45) Date of Patent: Nov. 3, 2020

(54) **PRODUCTION OF THAPSIGARGINS BY *THAPSIA* CELL SUSPENSION CULTURE**

(71) Applicant: Phyton Holdings, LLC, Fort Worth, TX (US)

(72) Inventors: Gilbert Gorr, Freiburg (DE); Harald Heckenmüller, Hamburg (DE); David Alexander Ullisch, Hamburg (DE); Jens Stefan Wilke, Hamburg (DE); Yantree Devi Sankar-Thomas, Tornesch (DE)

(73) Assignee: Phyton Holdings, LLC, Fort Worth, TX (US)

( * ) Notice: Subject to any disclaimer, the term of this patent is extended or adjusted under 35 U.S.C. 154(b) by 0 days.

(21) Appl. No.: 15/100,780

(22) PCT Filed: Dec. 2, 2014

(86) PCT No.: PCT/IB2014/002638
§ 371 (c)(1),
(2) Date: Jun. 1, 2016

(87) PCT Pub. No.: WO2015/082978
PCT Pub. Date: Jun. 11, 2015

(65) Prior Publication Data
US 2016/0312255 A1    Oct. 27, 2016

Related U.S. Application Data

(60) Provisional application No. 61/910,919, filed on Dec. 2, 2013.

(51) Int. Cl.
| | | |
|---|---|---|
| *C12P 17/04* | (2006.01) | |
| *C12N 5/04* | (2006.01) | |
| *C12N 5/00* | (2006.01) | |
| *C12P 5/00* | (2006.01) | |
| *A01H 4/00* | (2006.01) | |

(52) U.S. Cl.
CPC ............ *C12P 17/04* (2013.01); *A01H 4/005* (2013.01); *C12N 5/0025* (2013.01); *C12N 5/04* (2013.01); *C12P 5/007* (2013.01)

(58) Field of Classification Search
None
See application file for complete search history.

(56) References Cited

U.S. PATENT DOCUMENTS

2012/0225936 A1* 9/2012 Steward ............... A61K 31/365
514/468

OTHER PUBLICATIONS

Smitt et al., 1996, In: Biotechnology in Agriculture and Forestry, vol. 37, Medicinal and Aromatic Plants IX, ed. Y.P.S. Bajaj, Springer-Verlag Berlin, pp. 402-409.*
Smetanska, 2008, Adv. Biochem. Engin./Biotechnol. 111: 187-228.*
Rasmussen et al., 1981, Planta Medica 43: 336-341.*
Smitt et al., 1995, Botanical Journal of the Linnean Society 117: 281-292.*
Gantet et al., 1998, Plant & Cell Physiology 39: 220-225.*
Smitt et al., XXIV *Thapsia garganica* L.: In Vitro Culture, Somatic Embryogenesis, and the Production of Thapsigargins. Biotechnology in Agriculture and Forestry. 1996;37:402-409.
Jäger et al., Somatic embryogenesis in cell cultures of Thapsia garganica: Correlation between the state of differentiation and the content of thapsigargins. Plant Cell Rep. Jul. 1993;12(9):517-20. doi:10.1007/BF00236099.
Dodonova et al., Suspension Culture of Artemisia Glabella Kar. Et Kir.—A Source for Sesquiterpene Lactone Arglabin. Processes of Culturing Microorganisms and Tissues—Producers of Physiologically Active Substances. Third International Congress, Moscow. 2005:80.
Dodonova et al.. Herald of the Karaganda University. 2010:22-28.
Dodonova, Arglabin synthesis activation in a suspension culture of artemisia glabella. Herald of the Karaganda University. 2010;1(57):23-28.

* cited by examiner

*Primary Examiner* — Bratislav Stankovic
(74) *Attorney, Agent, or Firm* — Wolf, Greenfield & Sacks, P.C.

(57) ABSTRACT

The present invention relates to a method of producing sesquiterpene lactones of the thapsigargin family, the method comprising the steps of: (a) culturing plant cells of the genus *Thapsia* in a nutrient medium in a suspension cell culture, wherein the cells produce one or more sesquiterpene lactones of the thapsigargin family; and (b) recovering one or more sesquiterpene lactones of the thapsigargin family produced in (a). The present invention further relates to a suspension cell culture comprising plant cells of the genus *Thapsia*, wherein the plant cells are capable of producing one or more sesquiterpene lactones of the thapsigargin family and to a plant cell biomass comprising plant cells of the genus *Thapsia* obtained from said suspension cell culture.

7 Claims, 2 Drawing Sheets

Standard:

Sample:

PRODUCTION OF THAPSIGARGINS BY *THAPSIA* CELL SUSPENSION CULTURE

RELATED APPLICATIONS

This application is a national stage filing under 35 U.S.C. § 371 of international PCT application PCT/IB2014/002638, filed Dec. 2, 2014, which claims priority to U.S. Provisional Application No. 61/919,919, filed Dec. 2, 2013. Each of the prior applications is incorporated by reference in its entirety.

FIELD OF THE INVENTION

The present invention relates to a method of producing sesquiterpene lactones of the thapsigargin family, the method comprising the steps of: (a) culturing plant cells of the genus *Thapsia* in a nutrient medium in a suspension cell culture, wherein the cells produce one or more sesquiterpene lactones of the thapsigargin family; and (b) recovering one or more sesquiterpene lactones of the thapsigargin family produced in (a). The present invention further relates to a suspension cell culture comprising plant cells of the genus *Thapsia*, wherein the plant cells are capable of producing one or more sesquiterpene lactones of the thapsigargin family and to a plant cell biomass comprising plant cells of the genus *Thapsia* obtained from said suspension cell culture.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

BACKGROUND

Plants contain a wide range of chemical compounds including pharmaceuticals. In many cases such secondary metabolites have been investigated for a pharmaceutical activity. The most prominent example is the anti-cancer compound paclitaxel which is expressed by members of the genus *Taxus*. Since many years, products are marketed which contain paclitaxel as the active pharmaceutical ingredient. Paclitaxel has been shown to kill highly proliferating human cells—fast cell growth is characteristic for many tumors—efficiently.

Naturally occurring thapsigargins, which belong to the chemical class of sesquiterpene lactones, have been investigated for their cell death inducing activity. It has been found that members of the thapsigargin family of sesquiterpene lactones act as apoptosis inducers in a proliferation independent manner. It was discovered that thapsigargin (FIG. 1), one distinct member of the thapsigargin family, is a specific inhibitor of the sarco-endoplasmic reticulum calcium transport ATPase (SERCA) family, thus suggesting a possible use in the fight against cancer. In order to target thapsigargin to cancer cells, such as e.g. prostate cancer cells, it can be conjugated to peptides which act as selective substrates for cancer cell-specific proteolytic enzymes, such as e.g. prostate specific antigen (PSA) [S B Christensen et al. 2009, Anti-Cancer Agents in Medicinal Chemistry; 9: 276-294]. Such a so-called prodrug comprising thapsigargin as the cytotoxic compound is currently under clinical development.

Thapsigargin family members are usually isolated from plants of the genus *Thapsia* such as for example *Thapsia garganica, Thapsia transtagana* and *Thapsia villosa* or any of the *Thapsia* plants referred to in Table 2. The distribution of thapsigargins in the different members of the genus *Thapsia* might vary. The most prominent compound—thapsigargin—has been originally isolated from *Thapsia garganica* but has been identified in other members of the genus *Thapsia* as well.

At present *Thapsia garganica* plants are the only commercially reasonable source for the compound thapsigargin because due to the complex chemical structure of this compound, it cannot be chemically synthesized at an economically reasonable price. In vitro cultures for the production of valuable plant-derived secondary metabolites have long been recognized as an alternative source. Scalability of in vitro cultures would allow commercial supply of a given compound at high quantities in a sustainable manner and independent from the natural environment.

Jäger et al. [Jäger et al. 1993; Plant Cell Reports: 12, 517-520] investigated *Thapsia* species grown in vitro as an alternative source for the production of thapsigargins. When they investigated differentiated in vitro plant material that was grown on solid media i.e. green cotyledonary embryos, shoots and roots the authors identified the pentaoxygenated thapsigargins nortrilobolid and trilobolid in said plant material. However, no hexaoxygenated thapsigargins have been identified. See also Smitt et al. 1996 [Smitt, U W, Jäger, A K, and Nyman, U; XXIV *Thapsia garganica* L.: In vitro culture, somatic embryogenesis, and the production of Thapsigargins; In: Biotechnology in Agriculture and Forestry, Vol 37; Medicinal and Aromatic Plants IX (ed. By Y P S Bajaj); Springer-Verlag Berlin Heidelberg 1996].

Moreover, when using other in vitro material such as callus, proembryogenic clusters or globular stage embryos grown on either solid medium or in suspension culture, no sesquiterpene lactones of the thapsigargin family were identified by these authors at all.

Thus, despite the fact that a lot of effort has been invested into methods to establish plant cell cultures for the production of thapsigargins, no method exists so far that enable the economic and simple production of these compounds from plant cell cultures, particularly cultures suitable for large scale approaches. Accordingly, there is still a need to provide such methods and such cell cultures.

This need is addressed by the provision of the embodiments characterised in the claims.

SUMMARY OF THE INVENTION

The present invention provides for various methods of producing sesquiterpene lactones of the thapsigargin family from a plant cell culture. One objective of the invention is to obtain commercially significant amounts of the end product from suspension cultures.

The invention thus provides for a method of producing one or more sesquiterpene lactones of the thapsigargin family from suspension cell culture by culturing plant cells of the genus *Thapsia* in a nutrient medium to form a cell culture that produces one or more thapsigargins, and recovering one or more thapsigargins.

Preferably, the plant cells are *Thapsia* cells. More preferably, the plant cells are selected from the group consisting of cells from *Thapsia garganica, Thapsia villosa, Thapsia transtagana, Thapsia gymnesica, Thapsia maxima, Thapsia decussate, Thapsia laciniata,* including the sub-species/varieties *Thapsia garganica* ssp. *decussata* var. *angusta,*

*Thapsia villosa* Var. *dissecta*, *Thapsia villosa* Var. *microcarpa* and *Thapsia villosa* Var. *stenoptera*. Even more preferably, the cells are undifferentiated cells, de-differentiated cells or meristematic cells or mixtures thereof but not embryogenic cells.

It is further preferred that the plant cells are cultured in a growth medium. More preferably, the growth medium is capable of inducing a growth increase of at least 50% in one week. Alternatively, or additionally, the plant cells are cultured in a production medium. Even more preferably, the plant cells are cultured in a growth medium and then subsequently cultured in a production medium. Preferably, the growth and the production media are different. It is further preferred that the growth medium does not comprise the plant growth regulator 2,4-D and/or that the production medium does not comprise the plant growth regulator 2,4-D.

DETAILED DESCRIPTION OF THE INVENTION

The present invention relates to a method of producing sesquiterpene lactones of the thapsigargin family, the method comprising the steps of: (a) culturing plant cells of the genus *Thapsia* in a nutrient medium in a suspension cell culture, wherein the cells produce one or more sesquiterpene lactones of the thapsigargin family; and (b) recovering one or more sesquiterpene lactones of the thapsigargin family produced in (a).

Figure 1:
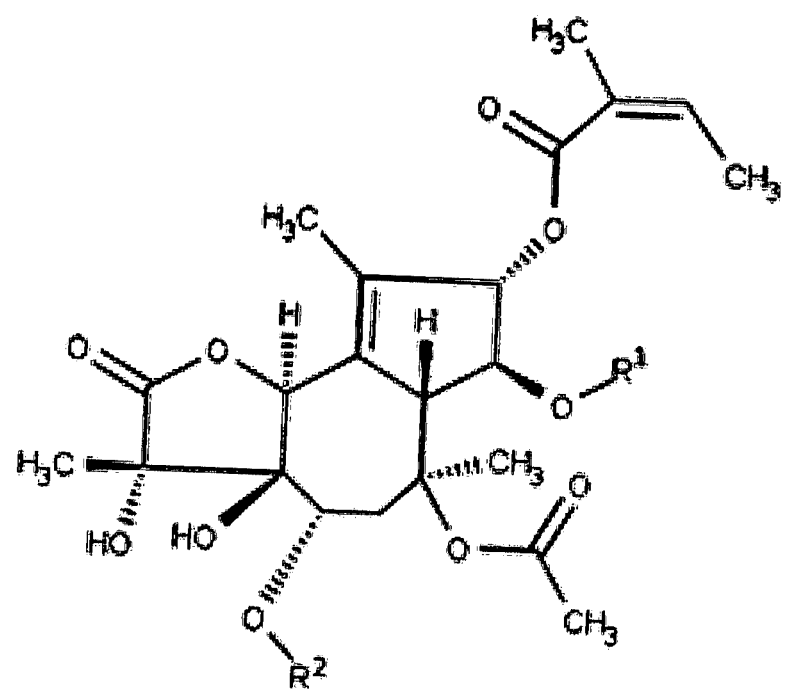
FIG. 1: General core structure of hexaoxygenated sesquiterpene lactones of the thapsigargin family, for detailed summary of substituents R1 and R2 see Table 1.
Figure 2:
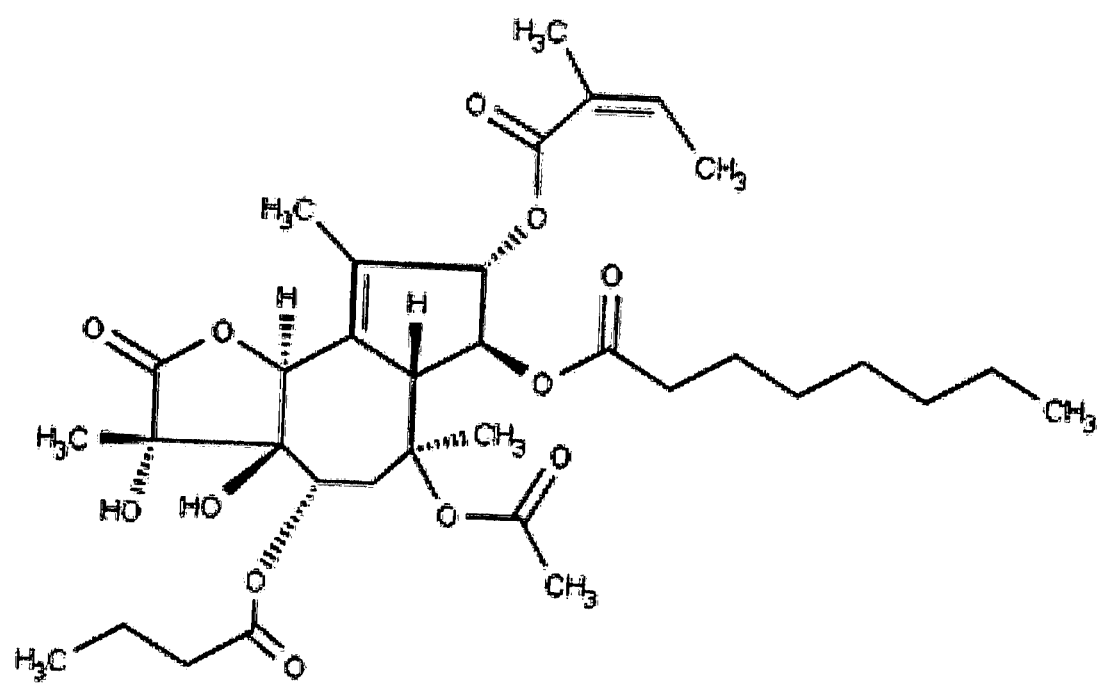
FIG. 2: Molecular structure of Thapsigargin.

The term "sesquiterpene lactones of the thapsigargin family", used interchangeable herein with the term "thapsigargins", refers to any member of the superfamily of guaianolides comprising a 2β,3α,7β,8α,10β,11α-hexaoxygenated-6β,12-guaianolide nucleus, i.e. the hexaoxygenated thapsigargins (FIG. 1), or a 3α,7β,8α,10β,11α-pentaoxygenated-6β,12-guaianolide nucleus, i.e. the pentaoxygenated thapsigargins. A characteristic feature of the sesquiterpene lactones of the thapsigargin family is the 7β-hydroxy group resulting in a trans-annelation of the lactone ring. Non-limiting members of the thapsigargin family are the hexaoxygenated thapsigargins differing in the structure of the acyl groups attached to O(2) and O(8) like thapsigargin (FIG. 2), thapsigargicin, thapsitranstagin, thapsivillosin A, thapsivillosin B, thapsivillosin C, thapsivillosin D, thapsivillosin E, thapsivillosin G, thapsivillosin H, thapsivillosin I, thapsivillosin J and thapsivillosin K and the pentaoxygenated thapsigargins differing in the structure of the acyl groups attached to O(8) like trilobolide, nortrilobolide and thapsivillosin F [Christensen et al. 1997; 129-167; in Progress in the Chemistry of Organic Natural Compounds; Ed. Herz, Kirby, Moore, Steglich and Tamm; Springer-Verlag Wien; ISBN 3-211-82850-8].

TABLE 1

Exemplary sesquiterpene lactones of the thapsigargin family. CAS Registry Numbers as assigned by the Chemical Abstracts Service are indicated where available. Oct = octanoic acid, But = butyric acid, Hex = hexanoic acid, 2-MeBut = 2-methylbutyric acid, 6-MeOct = 6-methyloctanoic acid, Sen = senecioic acid, Ang = angelic acid, 6-MeHep = 6-methylheptanoic acid, iVal = Isovaleric acid 3-methylbutanoic acid, according to Christensen et al. 2009 [SB Christensen et al. 2009, Anti-Cancer Agents in Medicinal Chemistry; 9: 276-294]

| Name (hexaoxygenated thapsigargins) | CAS Reg. No./(substitution pattern) |
|---|---|
| Thapsigargin | 67526-95-8/($R^1$ = Oct/$R^2$ = But) |
| Thapsigargicin | 67526-94-7/($R^1$ = Hex/$R^2$ = But) |
| Thapsitranstagin | 81127-21-1/($R^1$ = iVal/$R^2$ = 2-MeBut) |
| Thapsivillosin A | 81127-16-4/($R^1$ = Ang/$R^2$ = Sen) |
| Thapsivillosin B | 81127-17-5/($R^1$ = Ang/$R^2$ = 2-MeBut) |
| Thapsivillosin C | —/($R^1$ = Oct/$R^2$ = 2-MeBut) |
| Thapsivillosin D | —/($R^1$ = 6-MeOct/$R^2$ = Sen) |
| Thapsivillosin E | 81127-19-7/($R^1$ = 6-MeOct/$R^2$ = 2-MeBut) |
| Thapsivillosin G | —/($R^1$ = 6-MeHep/$R^2$ = 2-MeBut) |
| Thapsivillosin H | —/($R^1$ or $R^2$ = Ang or Sen) |
| Thapsivillosin I | 94567-55-2/($R^1$ = Ang/$R^2$ = But) |
| Thapsivillosin J | —/($R^1$ = iVal/$R^2$ = But) |
| Thapsivillosin K | —/($R^1$ = Sen/$R^2$ = 2-MeBut) |

| Name (pentaoxygenated thapsigargins) | CAS Reg. No./substitution pattern |
|---|---|
| Trilobolide | 50657-07-3/($R^1$ = Desoxy/$R^2$ = 2-MeBut) |
| Nortrilobolide | 136051-63-3/($R^1$ = Desoxy/$R^2$ = But) |
| Thapsivillosin F | —/($R^1$ = Desoxy/$R^2$ = Sen) |

Preferably, the sesquiterpene lactone of the thapsigargin family is a sesquiterpene lactone of the thapsigargin family capable of being produced from a *Thapsia* cell. Even more preferably, the sesquiterpene lactone of the thapsigargin family capable of being produced from a *Thapsia* cell is the compound thapsigargin.

It is also preferred that the sesquiterpene lactone of the thapsigargin family possesses therapeutic activity, or that it can be modified to yield bioactive compounds. Bioactive compounds are characterized in that they comprise a sesquiterpene lactone of the thapsigargin family possessing therapeutic activity fused to a targeting peptide as described for example in [U.S. Pat. No. 7,468,345]. In a preferred embodiment, the sesquiterpene lactone of the thapsigargin family itself possesses therapeutic activity and can be targeted to a certain environment in the human or animal body by fusion to a targeting peptide which is cleaved off specifically in said environment of the human or animal body by for example, but not limited to, a protease.

The term comprising, as used herein, denotes that further steps and/or components can be included in addition to the specifically recited steps and/or components. However, this term also encompasses that the claimed subject-matter consists of exactly the recited steps and/or components.

In accordance with the present invention, cells producing sesquiterpene lactones of the thapsigargin family are cultured to produce one or more sesquiterpene lactones of the thapsigargin family, as defined above. The term "cells producing sesquiterpene lactones of the thapsigargin family" refers to any cells capable of producing one or more sesquiterpene lactones of the thapsigargin family under at least one set of culture conditions. In accordance with the present invention, the "cells producing sesquiterpene lactones of the thapsigargin family" are cells which produce one or more sesquiterpene lactones of the thapsigargin family in a detectable amount under the culture conditions as defined in the method of the invention.

In accordance with the method of the invention, the cell culture comprises cells of the genus *Thapsia*. Plants of the genus *Thapsia* include, without being limiting *Thapsia garganica*, *Thapsia villosa*, *Thapsia transtagana*, *Thapsia gymnesica*, *Thapsia maxima*, *Thapsia decussate*, *Thapsia laciniata*, including the sub-species/varieties *Thapsia garganica* ssp. *decussata* var. *angusta*, *Thapsia villosa* Var. *dissecta*, *Thapsia villosa* Var. *microcarpa* and *Thapsia villosa* Var. *stenoptera*, as shown in Table 2 below. In a preferred embodiment of the method of the invention, the plant cells of the culture are selected from the group consisting of *Thapsia garganica* cells, *Thapsia gymnesica* cells and *Thapsia villosa* cells. In a more preferred embodiment of the method of the invention, the cell culture comprises *Thapsia garganica* cells.

TABLE 2

Exemplary cell species useful for production of sesquiterpene lactones of the thapsigargin family

| Genus | Exemplary Species | Exemplary Sub-Species/Varieties |
|---|---|---|
| Thapsia | T. garganica | |
| | T. villosa | |
| | T. transtagana | |
| | T. gymnesica | |
| | T. maxima | |
| | T. decussata | |
| | T. laciniata | |
| | T. garganica | ssp. decussate var. angusta |
| | T. villosa | Var. dissects |
| | | Var. microcarpa |
| | | Var. stenoptera |

For example, the cells in one and the same suspension cell culture can be from one or more species, sub-species, varieties, or strains. Preferably, the cells are from one species, more preferably from one sub-species, even more preferably from one variety and most preferably from one strain.

The plant tissue used to initiate the suspension cell culture can be any plant tissue, preferably a tissue selected based on, for example, the ability to favor the production of one or more particular sesquiterpene lactones of the thapsigargin family. Non-limiting examples of tissue for use in initiating the suspension culture are cells obtained from plant parts, such as e.g. roots, leaves, stems, meristems or cells obtained from a previously formed callus, preferably from friable callus material. The plant cells can be cells obtained directly from a plant or cryopreserved cells.

The method includes a step of culturing the suspension culture in a nutrient medium. The method can also include more than one step of culturing the suspension culture in a nutrient medium.

In accordance with the present invention, a nutrient medium is employed. The term "nutrient medium", as used herein, refers to a medium that is suitable for the cultivation of plant cell calli and/or suspension cultures. The term "nutrient medium" encompasses both "growth medium" and "production medium". The term "growth medium" refers to a nutrient medium that favors the growth of cultured cells. In a preferred embodiment, the growth medium provides a growth increase of at least 50% in one week. Preferably but not exclusively, the growth increase is determined based on dry weight. More preferably, the growth increase is determined on fresh weight. A "production medium", in accordance with the present invention, is a nutrient medium that favors the production of one or more sesquiterpene lactones of the thapsigargin family. It will be appreciated that growth can also occur in a production medium and that production can take place in a growth medium, such that the growth and the production medium may be identical. More preferably, however, a production medium is chosen that favors the production of target compounds to a greater extent than the growth medium employed.

It is well known in the art that cell growth is generally favored by a balanced or relatively low ratio of carbon to inorganic components such as nitrogen and phosphate, while cell growth is limited by a relatively high ratio of carbon to inorganic components. Accordingly, the production medium may utilize growth limiting conditions, e.g., a high ratio of carbon to inorganic components, to promote sesquiterpene lactone of the thapsigargin family production as opposed to cell growth [see e.g. Majerus F. & Pareilleux A., "Alkaloid accumulation in Ca-alginate entrapped cells of *Catharanthus roseus:* Using a limiting growth medium", Plant Cell Reports (1986) 5: 302-305].

Nutrient media are well established in the art and can be based, for example, on Murashige and Skoog Basal Salts (MS), Schenk and Hildebrandt Basal Salts (SH) or a compound composition according to Gamborg (B5).

Exemplary production media (PM) include, but are not limited to, media containing a salt base (e.g., MS or SH), plus macronutrients, micronutrients, vitamins, and a carbon source, preferably sucrose.

Preferred amounts of sucrose to be employed are between 0.01% and 10%, more preferably between 0.05 and 8.%, more preferably between 0.5 and 6%, such as e.g. between 1% and 4% and most preferably the amount is about 3%. Sucrose may be obtained from e.g. Sigma Aldrich, Carl Roth and/or VWR. Preferred amounts of nitrogen to be employed are between 0.1% and 10%, more preferably between 0.5% and 5% such as e.g. between 1% and 3% and most preferably 2.63%. Nitrogen may be obtained from nitrate, ammonium and amino acids.

Exemplary growth media include, but are not limited to, media containing a salt base (e.g., MS or SH or B5), plus a carbon source, preferably sucrose.

Preferred amounts of sucrose to be employed are between 0.01% and 6%, more preferably between 0.1 and 5%, such as e.g. between 1% and 3% and most preferably the amount is about 2%. Sucrose may be obtained from e.g. Sigma Aldrich, Carl Roth and or VWR. Preferred amounts of nitrogen to be employed are between 0.1% and 10%, more preferably between 0.5% and 5% such as e.g. between 1% and 3% and most preferably 2.63%. Nitrogen may be obtained from nitrate, ammonium and amino acids.

Thus a preferred growth medium contains a salt base (e.g., MS or SH or B5), plus 2% sucrose.

Suspension cultures producing sesquiterpene lactones of the thapsigargin family are capable of rapid growth rates and high cell densities when suitable nutrients and reaction conditions are used. One of ordinary skill in the art can readily incorporate, modify, and manipulate media conditions in view of the guidance provided herein and available from the art to achieve optimum performance, which may vary between cell lines.

The production of secondary metabolites in plant suspension cultures is known to be influenced by plant growth regulators, likewise, in the culture medium for sesquiterpene lactone of the thapsigargin family production, omitting or lowering the content of plant growth regulators substances may improve production. Improvement of sesquiterpene lactone of the thapsigargin family production by selected plant growth regulators can be experimentally confirmed by the skilled person without further ado.

The rate of production of thapsigargins is determined not by a single rate-limiting step, but by a complex interaction between a plurality of limiting factors. Relief of any one of the limiting factors will enhance production of thapsigargins, although the magnitude of the enhancement will depend on the particular culture conditions, which determine the relative limiting effects of other steps in the production of thapsigargins once a particular limitation has been relieved. Culture conditions that affect the interaction between various limiting factors include: the genetic make-up of the cells; the composition of the culture medium, and the temperature.

Plant growth regulators include a wide variety of substances readily known from the general plant literature. Of these, growth regulators particularly suitable for *Thapsia* suspension cultures include, without being limiting, auxin and/or cytokinin-like compounds, e.g., indoleacetic acid, indolebutyric acid, naphthalene acetic acid (NAA), picloram, dicamba, benzylaminopurine, kinetin, zeatin, thidiazuron, and indole acetic acid. Amino acids include any natural or synthetic amino acid utilized by the cells such as glutamine, glutamic acid, and aspartic acid. These can be used singly or in any combination. Preferably, a combination of dicamba, benzylaminopurine and thidiazuron are employed, as shown in the appended examples.

As the plant growth regulator 2,4-Dichlorophenoxyacetic acid is known for its impact on inititiation of embryogenesis in *Thapsia* suspension cultures, nutrient media free of 2,4-Dichlorophenoxyacetic acid are most preferred, in order to maintain the plant cells in a non-embryogenic state.

It is also desirable to reduce or avoid oxidative browning in the cell culture. Thus, anti-browning agents may be added to inhibit the oxidation of phenolic exudates. Preferably, the suspension cultures are undifferentiated cells, which are less susceptible to browning than embryonic cells.

Suggested concentration ranges for these medium components are provided below, but routine optimization may demonstrate preferred conditions outside these ranges for particular cell lines and/or particular culture conditions. All concentrations refer to average initial values in the extracellular medium after addition. Concentrations in feed solutions and therefore, locally, concentrations in contact with the cells could be higher than that indicated. Preparations containing cellular material can be added based on the concentration of a specific constituent of the preparation or as some fraction of the culture volume.

Plant growth regulators can be used at concentrations of about 0.001 μmol/L to about 2 mmol/L, preferably about 0.01 μmol/L to about 1 mmol/L.

Amino acids can be used at concentrations of about 1 μmol/L to about 20 mmol/L, preferably about 10 μmol/L to about 10 mmol/L.

Using these suggested concentrations as a guide, routine optimization can discern which component, or combination of components, and which concentrations, including concentrations beyond the suggestions above, are useful to maximize sesquiterpene lactones of the thapsigargin family production.

In a preferred embodiment, the cells are first cultured in a growth medium, and then the cells are cultured in a production medium that is different from the growth medium. The growth medium also comprises sources of inorganic or organic nitrogen such as an amino acid. When cells are transferred from a growth medium to a production medium, the production medium preferably has a higher level of carbon source and/or C:N ratio, e.g., a higher concentration of a saccharide. The production medium also preferably comprises sources of inorganic or organic nitrogen such as an amino acid. Other components of the nutrient medium can be introduced into the culture after the cells and medium are first contacted. In one embodiment, these ingredients, such as additional saccharide, are supplied in a feed stream intermittently or continuously as needed.

It will be appreciated that the method of the invention can include one or more steps of culturing the cells in a growth medium and/or one or more steps of culturing the cells in a production medium.

General cell culture conditions are well known in the art and it is known that the desired effect, e.g., growth or production, can be achieved by manipulating the media conditions described above by adding, removing, or changing the concentration of one or more nutrients or other agents. In addition to modifying the medium components, other reaction conditions can also be modified to obtain the desired result, for example by manipulating conditions including, but not limited to, temperature and pH or by manipulating any combination of these conditions.

For example, the temperature range can be adjusted. Preferred temperatures include about 0° C. to about 40° C., more preferably about 15° C. to about 35° C., and even more preferably about 20° C. to about 30° C. Even more preferably, the cell culture conditions comprise conditions of shaking, preferably at about 40 rpm to about 350 rpm, more preferably about 80 rpm to about 200 rpm such as e.g. between about 100 rpm and about 150 rpm, even more preferably about 130 rpm and most preferably the shaking frequency is 130 rpm, in darkness at a temperature of about 23° C. to 27° C., preferably about 25° C. Moreover, it is preferred that the cell cultures are sub-cultured every 14 days.

The term "about", as used herein, encompasses the explicitly recited values as well as small deviations therefrom. In other words, a shaking speed of "about 130 rpm" includes, but does not have to be exactly the recited amount of 130 rpm but may differ by several rpm, thus including for example 131 rpm, 132 rpm, 129 rpm, or 128 rpm. The skilled person is aware that such values are relative values that do not require a complete accuracy as long as the values approximately correspond to the recited values. Accordingly, a deviation from the recited value of for example 15%, more preferably of 10%, and most preferably of 5% is encompassed by the term "about".

In addition to the above, the general process operations can be adjusted without further ado by the skilled person. The operating mode for a plant cell culture process refers to the way that nutrients, cells, and products are added or removed with respect to time [Payne, G., et al., 1991; "Plant Cell and Tissue Culture in Liquid System", 62-66 & 298-297 (Hanser Publishers]. Ingredients provided to the cells can be provided in a number of different ways. Ingredients can be added in a particular stage of growth such as lag, exponential, or stationary. All ingredients can be provided at once and then after a suitable period of time, product can be recovered. In other circumstances, not all ingredients can be provided all at once. Rather, one or more of them may be provided at different times during the cultivation. Further, the additions can be discontinuous or staggered as to the time of initial contact and the duration of such provision can vary for different ingredients. Ingredients can be provided in a plurality of parts. One or more ingredients can be supplied as part of solutions separately contacted with the cell culture or portions thereof. Portions of the suspension culture can be removed at any time or periodically and used for cryopreservation, further cell propagation, production, and/or recovery. Such cell-containing portions can be exposed further to nutrients or other ingredients as desired. Exemplary subculture procedures are described herein.

In one embodiment, medium containing nutrients or other ingredients can be added to replenish a portion or all of the removed volume. Portions of such removed material can be added back into the original culture, for instance, cells and medium can be removed, a portion of the cells or medium can be used for product recovery and the remaining cells or medium can be returned. The supply rate of ingredients to the culture or levels of various ingredients in the culture can be controlled to advantageously produce and recover the product. Separate portions of the culture can be exposed to ingredients in any of the foregoing modes and then combined in proportions determined to be advantageous for production. Also the cell content of the culture can be adjusted to advantageously yield product or propagate cells. Adjustment of cell content can be advantageously combined with strategies for contacting with nutrients or other ingredients.

The replenishment of fresh medium to cells undergoing active biosynthesis may also enhance production by providing essential nutrients that have been depleted. For example, Miyasaka et al. were able to stimulate stationary phase cells of *Salvia miltiorhiza* to produce the diterpene metabolites cryptotanshinone and ferruginol simply by adding sucrose to the medium [Miyasaka et al., "Regulation of Ferruginol and Cryptotanshinone Biosynthesis in Cell Suspension Cultures of *Salvia miltiorrhiza*," Phytochemistry 25: 637-640 (1986)]. Presumably, biosynthesis had ceased due to carbon limitation in the stationary phase.

Using a periodic-medium-exchange protocol for the present culture method may provide similar benefits.

It is contemplated that the amount of medium exchanged, the frequency of exchange, and the composition of the medium being replenished can be varied in accordance with various embodiments of the invention. The ability to stimulate biosynthesis by medium exchange has important implications for the design and operation of an efficient commercial process in the continuous, semi-continuous, or fed-batch mode. In a "fed-batch" operation, particular medium components such as nutrients are supplied either periodically or continuously. In a preferred embodiment, a substantial portion, but not all, of the contents of a batch culture is replaced by fresh medium for continued cell growth and production; this process mode resembles a "repeated draw and fill" operation and is termed a "semi-continuous process." In an alternative, preferred embodiment, the process is "continuous," that is, fresh medium is continuously supplied, and effluent medium is continuously or repetitively removed.

The term "suspension culture", as used herein, refers to the culture of cells, preferably structurally undifferentiated cells, dispersed in a liquid nutrient medium. Due to this culture technique, the cells do not adhere to the solid support or the culture vessel. It is readily understood that suspension cultures comprise cells in various stages of aggregation. A range of aggregate sizes are encountered in the suspensions with sizes ranging from tens of microns in diameter (single cells or few-aggregated cells) to aggregates many millimeters in diameter, consisting of many thousands of cells. Suspension cultures comprising such aggregates are encompassed by the method of the present invention.

To transfer cells into a suspension culture, they are for example removed from a callus and transferred to sterile culture vessels containing nutrient medium. Suspension culture can, for example, be initiated using a nutrient medium that was successful in the previous generation of e.g. a friable callus culture, preferably without gelling agents. However, it is appreciated that optimized media for suspension culture may differ from the optimum for callus of the same cell line. The skilled person can determine suitable media without further ado.

Alternatively, or additionally, the plant cell culture may also be derived from a cryopreserved collection of cells.

Once initiated, a suspension culture can be further cultivated, either by (i) separating the cells substantially from the medium (typically by filtration) and then reintroducing a portion to a medium containing nutrients, or by (ii) transferring a volume of culture broth (cells and medium) into a medium containing nutrients, or by (iii) allowing the cells to settle followed by removal of any portion of medium already present and reintroducing nutrient-containing medium. When cells and media are transferred volumetrically, the ratio of the transferred volume to the final volume can be preferably from about 1% to substantially all of the volume, more preferably from about 5% to about 50% and even more preferably from 10% to about 20%. In the case all of the volume is transferred, fresh nutrients can be supplied in a concentrated form, resulting in only a small volume increase. The culture can thus be divided into portions, which can individually be further employed to either grow cells further, to produce thapsigargins or both. Each portion can, but need not, be cultured under the same conditions as one another or as the original culture. The duration of growth can be extended by supplementing a partially depleted medium with nutrients.

The cells grown in accordance with the method of the present invention produce one or more sesquiterpene lactones of the thapsigargin family, as defined above.

The term "one or more" as used herein, for example in the term "one or more sesquiterpene lactones of the thapsigargin family" refers to exactly one but also to more than one, such as e.g. two, three, four, five, six, seven and so on. Moreover, the term "one or more" does not define the actual number of one type of molecule present, but refers to the number of distinct molecules of the recited class. For example, the term "one or more sesquiterpene lactones of the thapsigargin family" refers to exactly one sesquiterpene lactone, such as e.g. the preferred sesquiterpene lactone thapsigargin, but also to more than one, such as e.g. two, three, four, five, six, seven etc. different sesquiterpene lactones of said family.

In the second step of the method of the present invention, the sesquiterpene lactone(s) of the thapsigargin family that has/have been produced by the cultured cells is/are recovered. The thapsigargins can be recovered from the entire culture or from any portion of culture, and they can be recovered at any time during the cultivation or after the completion of the culture period. It will be appreciated that all of the thapsigargins produced can be recovered, or, preferably, that one or more particular thapsigargins of interest are recovered, such as e.g. only hexaoxygenated thapsigargins, only pentaoxygenated thapsigargins or even only the single compound thapsigargin.

Cell material can be lyophilised in advance to the extraction procedure. Other methods known in the art can be used in order to prepare cell material or suspension material for the appropriate extraction method. Sesquiterpene lactones of the thapsigargin family can be recovered by any method known in the art including, without limitation, extraction using a non-aqueous polar solvent, extraction by using an acid medium, extraction by using a basic medium, recovery by resin absorption where the resin is either inside or outside of the culture vessel.

Methods of isolating the molecules produced are well-known in the art and comprise without being limiting method steps such as extraction of freeze dried cells or aqueous cell suspensions using organic solvents like e.g. ethyl acetate, acetone or toluene, followed by a subsequent chromatographic separation by using e.g. liquid chromatography (LC), reversed phase LC, or liquid/liquid chromatography. Where the sole sesquiterpene lactone to be recovered is the compound thapsigargin, it is preferred that it is recovered using purification sequences as described by e.g. Ollivier A et al. 2013 [Ollivier, A. 2013; J Chromatogr B Analyt Technol Biomed Life Sci.; 926: 6-20] or Rasmussen et al. 1978 [Rasmussen U. et al. 1978; Acta Pharm Suec.; 15(2); 133-40]

Preferably, recovering is performed as described in the appended examples, i.e. by lyophilising the biomass obtained in the cell culture and homogenising the lyophilised biomass with a solvent in a bead mill, followed by centrifugation to obtain a crude extract and purification of the components of the crude extract as described in Ollivier A et al. 2013 [Ollivier, A. 2013; J Chromatogr B Analyt Technol Biomed Life Sci.; 926: 6-20].

In accordance with the present invention, a novel method is provided for the production of sesquiterpene lactones of the thapsigargin family. By using cells grown in a suspension culture, mass production of thapsigargins is now possible, e.g. by semi-continuous or continuous cell culture techniques. To the inventor's best knowledge, no such plant cell culture approach for the mass production of thapsigargins is presently available. The lack of such methods currently presents a threat to the existence of plants of the *Thapsia* genus, which are at present the only feasible source for the isolation of thapsigargins in large amounts [S B Christensen et al. 2009, Anti-Cancer Agents in Medicinal Chemistry; 9: 276-294]. This is because synthetic methods of producing these compounds are not available from an economic point of view, as synthesis requires at least 42 steps.

In a preferred embodiment of the method of the invention, the one or more of the sesquiterpene lactones of the thapsigargin family recovered in step (b) comprises a 2β,3α,7β,8α,10β,11α-hexaoxygenated-6β,12-guaianolide nucleus.

As detailed above, the sesquiterpene lactones produced by the respective plant cells can be identical, i.e. they represent only one molecular type of sesquiterpene lactone, or they can be a mixture of different molecular types of sesquiterpene lactones. As also detailed above, all of these produced sesquiterpene lactones of the thapsigargin family may be recovered, or only preferred compounds from this group.

Thus, in accordance with this preferred embodiment, encompassed is that (i) one of the sesquiterpene lactones of the thapsigargin family recovered in step (b) in accordance with the method of the invention comprises a 2β,3α,7β,8α,10β,11α-hexaoxygenated-6β,12-guaianolide nucleus, (ii) a plurality but not all of the sesquiterpene lactones of the thapsigargin family recovered in step (b) in accordance with the method of the invention comprise a 2β,3α,7β,8α,10β,11α-hexaoxygenated-6β,12-guaianolide nucleus or (iii) all sesquiterpene lactones of the thapsigargin family recovered in step (b) in accordance with the method of the invention comprise a 2β,3α,7β,8α,10β,11α-hexaoxygenated-6β,12-guaianolide nucleus.

In a more preferred embodiment of the method of the invention, the sesquiterpene lactone of the thapsigargin family comprising a 2β,3α,7β,8α,10β,11α-hexaoxygenated-6β,12-guaianolide nucleus is thapsigargin.

Thapsigargin is the most commonly used sesquiterpene lactone of the thapsigargin family and its structure is shown in FIG. 1. Preferably, thapsigargin is the sole sesquiterpene lactone of the thapsigargin family recovered from the plant cells in accordance with the method of the invention.

In another preferred embodiment of the method of the invention, the one or more of the sesquiterpene lactone of the thapsigargin family recovered in step (b) comprises a 3α,7β,8α,10β,11α-pentaoxygenated-6β,12-guaianolide nucleus.

The same considerations as with regard to the hexaoxygenated thapsigargins also apply to the pentaoxygenated thapsigargins, i.e. in accordance with this preferred embodiment, encompassed is that (i) one of the sesquiterpene lactones of the thapsigargin family recovered in step (b) in accordance with the method of the invention comprises a 3α,7β,8α,10β,11α-pentaoxygenated-6β,12-guaianolide nucleus, (ii) a plurality but not all of the sesquiterpene lactones of the thapsigargin family recovered in step (b) in accordance with the method of the invention comprise a 3α,7β,8α,10β,11α-pentaoxygenated-6β,12-guaianolide nucleus or (iii) all sesquiterpene lactones of the thapsigargin family recovered in step (b) in accordance with the method of the invention comprise a 3α,7β,8α,10β,11α-pentaoxygenated-6β,12-guaianolide nucleus.

From the above it is evident that also a mixture of hexaoxygenated thapsigargins and pentaoxygenated thapsigargins may be recovered.

In another preferred embodiment of the method of the invention, the plant cells are non-embryogenic cells.

In accordance with the present invention, the term "non-embryogenic cells" refers to undifferentiated, dedifferentiated and meristematic cells. The non-embryogenic cells can be distinguished from embryogenic cells by the presence of (a) vacuole(s), whereas embryogenic cells are highly cytoplasmic and non-vacuolated.

Means and methods to obtain non-embryogenic cells for use in the method of the invention are well known in the art. Non-limiting examples for obtaining non-embryogenic cells include, e.g. their derivation from a friable callus. To provide an example, an inoculum from such a friable callus of about 0.01 to about 10 g/25 ml can be employed to prepare non-embryogenic suspension cultures for use in the method in accordance with the present invention. In accordance with the present invention, the plant cells stay non-embryogenic during the suspension culture.

The term "friable callus material" refers to a substantially undifferentiated cell mass cultured on solidified medium. Methods for friable callus material formation and callus propagation are generally known in the art. Non-limiting methods for obtaining a callus include, for example, surface sterilizing plant source material, e.g., by washing thoroughly with clean water, using a disinfectant such as hypochlorite, using wetting agents such as Tween or Triton, using antibiotics, and/or using antifungal agents. Callus formation can be initiated from any viable part of the plant (also referred to herein as "plant explant"), preferably from root tissue of the plant. The plant source material can be an intact part of the plant, or a portion thereof. Typically, the plant source material is placed on the surface of solidified medium and incubated in a sterile environment for about 1-12 weeks, until a mass of undifferentiated cells (the friable callus material) grows in proximity to the plant source material.

After establishing the friable callus material, the cells are cultured in a nutrient medium in accordance with the method of the invention.

Culture conditions for friable callus propagation including media components, pH ranges, carbon sources, nitrogen sources, macro-salts and micro-salts, vitamins, and growth regulators are well known in the art and have been described, for instance, in WO 97/44476, incorporated in its entirety herein by reference. In a preferred embodiment, friable callus propagation comprises using a gelling agent. Gelling agents include, for example, agar, hydrogels, gelatin, and Gelrite®. Charcoal can be used for removing wastes and undesirable organic compounds. In another preferred embodiment, friable callus propagation comprises initiation of friable callus material on medium free of 2,4-Dichlorophenoxyacetic acid. In a further preferred embodiment, friable callus propagation comprises cultivation of friable callus on medium free of 2,4-Dichlorophenoxyacetic acid. The medium for initiation and propagation of friable callus for all embodiments of the present invention can be, e.g. a solid medium or a semi-solid medium. Preferably, the medium for initiation and propagation of friable callus for all embodiments of the present invention is a solid medium.

Sub-culturing techniques known in the art can be used for periodic serial transfer of portions of friable callus into a fresh source of nutrients. Preferably, the frequency of transferring calli is between 4 to 6 weeks.

As discussed herein above, the present invention provides for the first time a suspension cell culture suitable for the mass production of thapsigargins. Whereas prior art attempts at producing thapsigargins from cell cultures have been described (see Jäger et al. 1993 cited above), they did not provide the advantageous format of thapsigargin production from a suspension culture. Without wishing to be bound by theory, the present inventors observe that in the prior art cells were used obtained from calli that were induced in a manner that results in embryogenesis of the plant material, which may have a negative impact on the production of thapsigargins by cells obtained from said plant material.

In accordance with the above, the method further comprises in a further preferred embodiment that prior to step (a), an additional step (a-0) is carried out, said step comprising culturing *Thapsia* plant explants on medium, thereby obtaining friable callus material. The medium for initiation of friable callus for all embodiments of the present invention can be, e.g. a solid medium or a semi-solid medium. Preferably, the medium for initiation of friable callus for all embodiments of the present invention is a solid medium.

The definitions and preferred embodiments provided herein above apply mutatis mutandis.

In a particular preferred embodiment, the present invention provides a method of producing sesquiterpene lactones of the thapsigargin family, the method comprising the steps of:
(a) culturing plant cells of the genus *Thapsia* in a nutrient medium in a suspension cell culture, wherein the cells produce one or more sesquiterpene lactones of the thapsigargin family; wherein the cell culture conditions comprise conditions of shaking, preferably at 130 rpm, in darkness at a temperature of about 23° C. to 27° C., preferably about 25° C. and wherein the cell cultures are sub-cultured at regular intervals, preferably every 14 days; and
(b) recovering the sesquiterpene lactones of the thapsigargin family produced in (a).

In another preferred embodiment of the method of the invention, the nutrient medium is free of 2,4-Dichlorophenoxyacetic acid.

2,4-Dichlorophenoxyacetic acid (also referred to herein as 2,4-D) is a synthetic auxin, i.e. a plant hormone, that is commonly employed in plant research as a supplement in plant cell culture media, where it is e.g. used as a growth regulator for the induction and maintenance of callus material and for the cultivation of suspensions until they become embryogenic.

In order to avoid embryogenesis, suspension cultures are thus grown in nutrient medium free of 2,4-Dichlorophenoxyacetic acid in accordance with this preferred embodiment. In another preferred embodiment, suspension cultures are maintained in nutrient medium free of 2,4-Dichlorophenoxyacetic acid. In accordance with the present invention maintenance of suspension cultures is characterized in that cells are viable but are not growing significantly. In a further preferred embodiment, suspension cultures are propagated in nutrient medium free of 2,4-Dichlorophenoxyacetic acid.

As mentioned herein above, prior art attempts at producing thapsigargins from cell cultures have been described (see Jäger et al. 1993 cited above) but did not show any thapsigargin production from a suspension culture. Again without wishing to be bound by theory, the present inventors observe that in the prior art, cells were used that were obtained by culture techniques employing the plant hormone 2,4-D that results in embryogenesis of the plant material, which may have a negative impact on the production of thapsigargins by cells obtained from said plant material. The positive impact of 2,4-D on initiation of embryogenesis has been discussed and acknowledged. The addition of 2,4-D into culture media and the thus initiated embryogenesis may explain why these authors identified only pentaoxygenated thapsigargins and these only in further differentiated embryo stages i.e. cotyledonary stage, shoots and roots grown on solid media.

Accordingly, in a particularly preferred embodiment, the present invention thus provides a method of producing sesquiterpene lactones of the thapsigargin family, the method comprising the steps of:
(a) culturing non-embryogenic plant cells of the genus *Thapsia* in a nutrient medium free of 2,4-Dichlorophenoxyacetic acid in a suspension cell culture, wherein the cells produce one or more sesquiterpene lactones of the thapsigargin family; and
(b) recovering the sesquiterpene lactones of the thapsigargin family produced in (a).

In a most preferred embodiment, the present invention provides a method of producing sesquiterpene lactones of the thapsigargin family, the method comprising the steps of:
(a) culturing plant cells of the genus *Thapsia* in a nutrient medium free of 2,4-Dichlorophenoxyacetic acid in a suspension cell culture, wherein the cells produce one or more sesquiterpene lactones of the thapsigargin family; wherein the cell culture conditions comprise conditions of shaking, preferably at 130 rpm, in darkness at a temperature of about 23° C. to 27° C., preferably about 25° C. and wherein the cell cultures are sub-cultured at regular intervals, preferably every 14 days; and
(b) recovering the sesquiterpene lactones of the thapsigargin family produced in (a).

In another particularly preferred embodiment, the present invention provides a method of producing sesquiterpene lactones of the thapsigargin family, the method comprising the steps of:
(a-0) culturing *Thapsia* plant explants on medium, thereby obtaining friable callus material (a) culturing plant cells of the genus *Thapsia* obtained in step (a-0) in a nutrient medium free of 2,4-Dichlorophenoxyacetic acid in a suspension cell culture, wherein the cells produce one or more sesquiterpene lactones of the thapsigargin family; and
(b) recovering the sesquiterpene lactones of the thapsigargin family produced in (a).

In an even more preferred embodiment, the present invention provides a method of producing sesquiterpene lactones of the thapsigargin family, the method comprising the steps of:
(a-0) culturing *Thapsia* plant explants on medium free of 2,4-Dichlorophenoxyacetic acid, thereby obtaining friable callus material
(a) culturing plant cells of the genus *Thapsia* obtained in step (a-0) in a nutrient medium in a suspension cell culture, wherein the cells produce one or more sesquiterpene lactones of the thapsigargin family; and
(b) recovering the sesquiterpene lactones of the thapsigargin family produced in (a).

In an even more preferred embodiment, the present invention provides a method of producing sesquiterpene lactones of the thapsigargin family, the method comprising the steps of:
(a-0) culturing *Thapsia* plant explants on medium free of 2,4-Dichlorophenoxyacetic acid, thereby obtaining friable callus material
(a) culturing plant cells of the genus *Thapsia* obtained in step (a-0) in a nutrient medium free of 2,4-Dichlorophenoxyacetic acid in a suspension cell culture, wherein the cells produce one or more sesquiterpene lactones of the thapsigargin family; and
(b) recovering the sesquiterpene lactones of the thapsigargin family produced in (a).

In a most preferred embodiment, the present invention provides a method of producing sesquiterpene lactones of the thapsigargin family, the method comprising the steps of:
(a-0) culturing *Thapsia* plant explants on medium free of 2,4-Dichlorophenoxyacetic acid, thereby obtaining friable callus material
(a) culturing plant cells of the genus *Thapsia* obtained in step (a-0) in a nutrient medium free of 2,4-Dichlorophenoxyacetic acid in a suspension cell culture, wherein the cells produce one or more sesquiterpene lactones of the thapsigargin family; wherein the cell culture conditions comprise conditions of shaking, preferably at 130 rpm, in darkness at a temperature of about 23° C. to 27° C., preferably about 25° C. and wherein the cell cultures are sub-cultured at regular intervals, preferably every 14 days; and
(b) recovering the sesquiterpene lactones of the thapsigargin family produced in (a).

The present invention also relates to a suspension cell culture comprising plant cells of the genus *Thapsia*, wherein the plant cells are capable of producing one or more sesquiterpene lactones of the thapsigargin family. Preferably, these suspension cell cultures are cultured/produced/producible/provided according to any of the embodiments described herein above.

The definitions and preferred embodiment provided herein above with regard to the method of the invention apply mutatis mutandis also to this suspension cell culture of the present invention.

To the inventors' best knowledge, no suspension cell culture of plant cells of the genus *Thapsia* is available in the art that is capable of producing sesquiterpene lactones of the thapsigargin family. Based on the method of the present invention, such a suspension cell culture could be provided for the first time and is suitable for the mass production of one or more thapsigargins.

The present invention further relates to a plant cell biomass comprising plant cells of the genus *Thapsia* obtained or obtainable from the suspension cell culture of the invention.

Again, all definitions and preferred embodiment provided herein above with regard to the method of the invention apply mutatis mutandis also to this plant cell biomass of the present invention.

The term "biomass", as used herein, refers to the biological material making up the cell mass of the suspension culture. In other words, when the cells of the suspension cell culture are separated from the liquid medium, the biomass is obtained. Preferably, the biomass, as used according to the invention, comprises one or more sesquiterpene lactones from the thapsigargin family.

The biomass of the present invention represents a valuable source of thapsigargins. The biomass can be a freshly obtained biomass or can be a biomass that has been stored, e.g. in form of a frozen sample or lyophilised powder.

It will be appreciated that all method steps described herein are carried out in the described order, i.e. step (a) is carried out prior to step (b). Where an additional step (a-0) is included, this step is carried out first, prior to step (a). In other words, the claimed methods comprise (or consist of) a first step (a) and a subsequent step (b) or, alternative, a first step (a-0), a subsequent step (a) and third step (b) subsequent to step (a).

Unless otherwise defined, all technical and scientific terms used herein have the same meaning as commonly understood by one of ordinary skill in the art to which this invention belongs. In case of conflict, the patent specification, including definitions, will prevail.

As regards the embodiments characterised in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 9, 8 and 1 is clearly and unambiguously envisaged in view of the claim structure. The same applies for example to the combination of claims 9, 8, 7 and 1, etc.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive.

The examples illustrate the invention:

EXAMPLE 1

Surface Sterilization of Intact Plant Material

Roots of *Thapsia garganica* were washed with tap water thoroughly. Roots were cut into small cubes (plant explants) of approx. 3×3 cm. Plant explants were thoroughly washed in detergent and under running water for about 10 to 15 minutes. Surface sterilization of explants was carried-out aseptically by immersing explants in a 70% isopropyl alcohol (IPA) (v/v) solution containing 2-3 drops of Tween 20 for 1 minute (gently agitated during this time). Thereafter, plant explants were treated in a NaOCl solution (2.8 g/100 ml sodium hypochlorite) for 15 to 30 minutes. Subsequently explants were briefly rinsed with sterile distilled water 3 to 4 times to remove all traces of the sterilizing agents. After surface disinfection the explants were kept in covered Petri dishes in the laminar flow cabinet until ready to process to avoid dehydration. Before the explants were placed on the solid culture medium, the cut ends of explants were removed with a sterile scalpel and the explants were cut into smaller pieces of an appropriate size (0.5-1 cm).

EXAMPLE 2

Embryogenic Callus Induction on Solid Medium Containing 2,4-D

Plant explants were put on a solid modified basal media of Musharige and Skoog (half strength MS basal salt, 3% sucrose, 0.5 mg/l BAP and 0.5 mg/l 2,4-D). Cultures were then incubated in darkness in an incubator maintained at 25±2° C. After 6-8 weeks primary callus material was obtained. Explants cultivated on MS medium supplemented with 2,4-D turned into an embryogenic callus that further developed into different stages of somatic embryos with increasing cultivation time. The frequency of transferring of the embryogenic calli depended on the growth rate and ranged from 4-8 weeks.

EXAMPLE 3

Friable Callus Induction on Solid Medium Free of 2,4-D

Plant explants were put on two different solid modified basal media of Gamborg (full strength B5 basal salt, 2% sucrose, 5 mM picloram and 0.01 mM BAP or 1 mg/l Dicamba and 0.22 mg/l TDZ). Cultures were then incubated in darkness in an incubator maintained at 25±2° C. After 6-8 weeks primary callus material was obtained. Friable callus material was established from the explants cultivated on both modified B5 media without 2,4-D after 4-6 weeks. The frequency of transferring of the friable calli depended on the growth rate and ranged from 4-6 weeks.

EXAMPLE 4

Initiation of Suspension Cultures of *Thapsia garganica*

For the initiation of suspension cultures friable callus material (approximately 40-60 g/l) was transferred into modified liquid B5 medium free of 2,4-D as described above. The suspension cultures grew in larger cell aggregates and were cultivated in 250 ml Erlenmeyer flasks in 50 ml cultivation medium on a rotary shaker at 130 rpm in the dark. The cultivation temperature was 25±2° C. Further media modifications such as a higher initial sucrose concentration or a higher nitrate to ammonium ratio can be applied to receive finer suspended cell lines.

EXAMPLE 5

Maintenance of Suspension Cultures of *Thapsia garganica*

For maintenance of the suspensions, vacuum-filtrated biomass (40-60 g/l) was transferred into 50 ml fresh modified liquid B5 medium free of 2,4-D as described above. The cultures were maintained in 250 ml Erlenmeyer flasks on a rotary shaker at 130 rpm in the dark and were sub-cultured every 14 days. The cultivation temperature was 25±2° C. All established cultures were maintained for at least 3 months.

EXAMPLE 6

Extraction of Biomass of *Thapsia garganica*

Biomass of *Thapsia garganica* (either callus material or vacuum-filtrated biomass from suspensions) was transferred into liquid nitrogen directly after sampling to avoid intracellular cell metabolism. To make an extract, lyophilized biomass samples were weighed out and 15 times as much solvent was added. As solvents EtOAc, acetone or ethanol was used. The cells were homogenized for 90 sec in a bead mill and this mixture was subsequently centrifuged for 10 min (14.000 rpm) to receive the crude extract which was used for further analysis.

EXAMPLE 7

Extraction of Suspension

A sample of a suspension culture of *Thapsia garganica* was lyophilized and subsequently weighed out. The lyophilisate was resuspended in 15 times volume of the solvent. As solvents EtOAc, acetone or ethanol was used. This mixture was homogenized for 90 sec in a bead mill and subsequently centrifuged for 10 min (14.000 rpm) to receive the crude extract which was used for further analysis.

EXAMPLE 8

Analysis of Sesquiterpene Lactones of the Thapsigargin Family

The following method was used for the detection of sesquiterpene lactones of the thapsigargin family:
Column: C18, like e.g. Waters Acquity UPLC BEH C18, 2.1×50 mm; 1.7μ
Chromatograph: UPLC, like e.g. Waters Acquity UPLC, with binary pump
Solvent: A: 10 mmol Ammonium acetate buffer+0.1% Formic acid
B: Acetonitril+0.1% Formic acid

| Gradient: | | | | | | |
|---|---|---|---|---|---|---|
| Time (min): | 0.00 | 1.50 | 1.51 | 4.00 | 4.10 | 5.00 |
| % solvent A: | 20 | 20 | 5 | 5 | 20 | 20 |
| % solvent B: | 80 | 80 | 95 | 95 | 80 | 80 |

Run time: 5.00 min
Injection volume: 4 μL
Retention time: approximately 1.18 min (Thapsigargin)
Detector: Mass spectrometer, like e.g. Waters Quattro Premier
Detection: ESI+

Identification Thapsigargin m/z=668.4$(M+NH_4)^+$/551.4$(M-OAng)^+$/491.4$(M-HOAc-OAng)^+$ Conditions: Capillary Voltage: 2.5 kV Cone Voltage: 18 V Source Temp: 150° C.

Desolvation Temp: 400° C.

Figure 3:
FIG. 3: UPLC-MS/MS-spectra of *Thapsia garganica* biomass samples derived from non-embryogenic suspension cell culture and Thapsigargin standard analysed by UPLC/MS. Two daughter ions (first (standard) and third (sample) graph m/z=491 and second (standard) and fourth (sample) graph m/z=551) obtained from the mother ion of thapsigargin (m/z=668; $M+NH_4^+$) were detected above the noise level in samples derived from non-embryogenic suspension cell culture.
Figure 3:
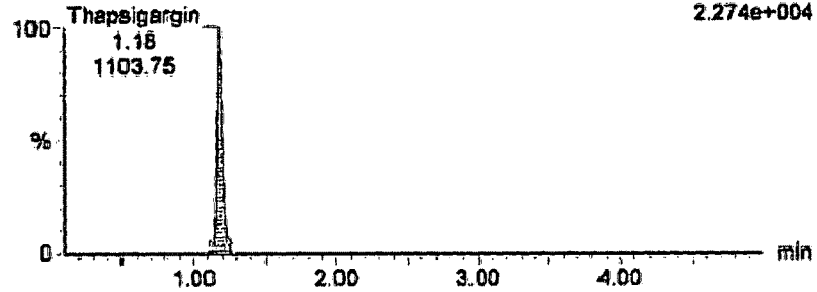
Figure 3:
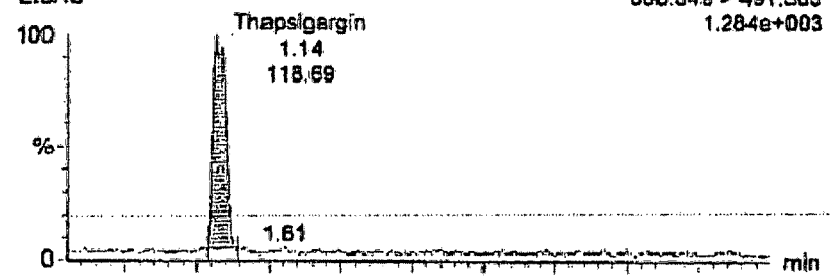
Figure 3:
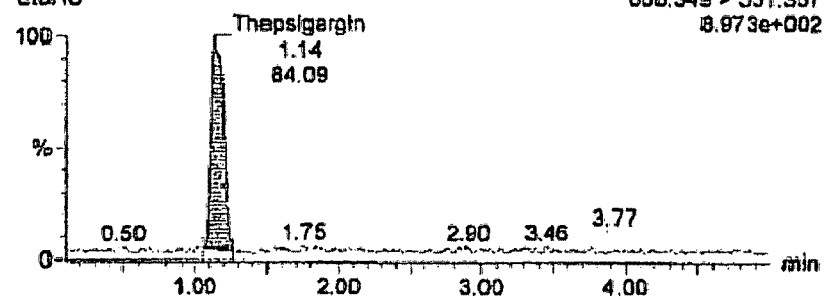

Applying these conditions to cell extracts described e.g. in example 7, Thapsigargin was clearly identified in the sample (see FIG. 3 sample) by comparison to a reference material (see FIG. 3 standard). For standard and sample the fragmentation of the mother ion at m/z=668 $(M+NH_4)^+$ into daughter ions at m/z=491 (upper graph in standard and sample) and m/z=551 (lower graph in standard and sample) was clearly observed.

EXAMPLE 9

Isolation of Thapsigargin and Other Sesquiterpene Lactones of the Tapsigargin Family Thapsigargin can be isolated from PCF cell suspensions using typical methods known in the art. Initial extraction of freeze dried cells or aqueous cell suspensions using organic solvents like e.g. ethyl acetate, acetone or toluene, is followed by a subsequent chromatographic separation using e.g. normal or reversed phase stationary phases. For examples of potential purification sequences see: Ollivier A, Grougnet R, Cachet X, Meriane D, Ardisson J, Boutefnouchet S, Deguin B. *J Chromatogr B Analyt Technol Biomed Life Sci.* 2013; 926; 16-20 or Rasmussen U, Brøogger Christensen S, Sandberg F. *Acta Pharm Suec.* 1978; 15(2); 133-40.

The invention claimed is:

1. A method of producing sesquiterpene lactones of the thapsigargin family, the method comprising the steps of:

(a) culturing non-embryogenic plant cells of the genus *Thapsia* in a nutrient medium in a suspension cell culture, wherein the cells produce one or more sesquiterpene lactones of the thapsigargin family, and wherein the nutrient medium is free of 2,4-Dichlorophenoxyacetic acid; and (b) recovering the one or more sesquiterpene lactone(s) of the thapsigargin family produced in (a);

wherein the one or more of the sesquiterpene lactones of the thapsigargin family comprises a 2β,3α,7β,8α,10β,11α-hexaoxygenated-6β,12-guaianolide nucleus.

2. The method of claim 1, wherein the sesquiterpene lactone of the thapsigargin family is thapsigargin.

3. The method of claim 1, wherein the plant cells are selected from the group consisting of *Thapsia garganica* cells, *Thapsia gymnesica* cells and *Thapsia villosa* cells.

4. The method of claim 1, further comprising prior to step (a) an additional step of:

(a-0) culturing *Thapsia* plant explants on medium, to obtain friable callus material and collecting the non-embryogenic plant cells therefrom.

5. The method of claim 1, wherein the nutrient medium in step (a) is a growth medium capable of inducing a growth increase of at least 50% in one week.

6. A suspension cell culture comprising non-embryogenic plant cells of the genus *Thapsia*, wherein the plant cells are capable of producing one or more sesquiterpene lactones of the thapsigargin family, wherein the one or more of the sesquiterpene lactones of the thapsigargin family comprises a 2β,3α,7β,8α,10β,11α-hexaoxygenated-6β,12-guaianolide nucleus.

7. A plant cell biomass comprising plant cells of the genus *Thapsia* obtained from the suspension cell culture of claim 6.

* * * * *